(12) United States Patent
Liou et al.

(10) Patent No.: US 9,775,875 B2
(45) Date of Patent: Oct. 3, 2017

(54) **METHOD OF PROCESSING *ZINGIBER ZERUMBET***

(71) Applicant: HAN SHENG PHARMTECH, INC., Pingtung County (TW)

(72) Inventors: Shorong-Shii Liou, Pingtung County (TW); I-Min Liu, Pingtung County (TW); Cheng Yang, Pingtung County (TW); Sheng-Da Lin, Pingtung County (TW); Chi-Da Fang, Pingtung County (TW); Bo-Wei Lin, Pingtung County (TW); Wan-Ling Huang, Pingtung County (TW); Ya-Ting Shiu, Pingtung County (TW)

(73) Assignee: HAN SHENG PHARMTECH, INC., Pingtung County (TW)

( * ) Notice: Subject to any disclaimer, the term of this patent is extended or adjusted under 35 U.S.C. 154(b) by 158 days.

(21) Appl. No.: 14/725,327

(22) Filed: May 29, 2015

(65) Prior Publication Data

US 2016/0346345 A1    Dec. 1, 2016

(51) Int. Cl.
*A61K 36/9068*    (2006.01)

(52) U.S. Cl.
CPC ...... *A61K 36/9068* (2013.01); *A61K 2236/00* (2013.01)

(58) Field of Classification Search
CPC .................................................. A61K 36/9068
USPC ........................................................ 424/756
See application file for complete search history.

(56) References Cited

FOREIGN PATENT DOCUMENTS

CN         1437971 A    *    8/2003

* cited by examiner

*Primary Examiner* — Chris R Tate
*Assistant Examiner* — Deborah Davis
(74) *Attorney, Agent, or Firm* — WPAT, P.C., Intellectual Property Attorneys; Anthony King

(57) ABSTRACT

The invention discloses a method of processing *Zingiber zerumbet* for producing a processed sample of *Zingiber zerumbet*, which easily releases flavonoids in a following extraction process. The method includes the steps of: soaking a raw sample of *Zingiber zerumbet* with a processing reagent selected from rice vinegar or yellow wine at 23-27° C. for 20-28 hours; and steaming the soaked product at 0.6-1.4 kg/cm$^2$, 80-120° C. for 20-40 minutes.

3 Claims, 2 Drawing Sheets

METHOD OF PROCESSING *ZINGIBER ZERUMBET*

BACKGROUND OF THE INVENTION

1. Field of the Invention

The present invention generally relates to a method of processing *Zingiber zerumbet* and, more particularly, to a method of processing *Zingiber zerumbet* for producing a processed sample of *Zingiber zerumbet*, which easily releases flavonoids in a following extraction process.

2. Description of the Related Art

*Zingiber zerumbet*, belonging to the ginger family, is usually used as food flavoring and appetizers in various cuisines. *Zingiber zerumbet* is also applied to treating toothache, indigestion and diarrhea, as well as increasing circulation of the blood.

The fresh rhizomes of *Zingiber zerumbet* are generally pounded or grounded to obtain the pulp or the juice for further application. Alternatively, the rhizome-containing flavonoids can also be extracted via the extraction process. However, the said extract has a low flavonoids level. In light of this, it is necessary to provide a method of processing *Zingiber zerumbet*.

SUMMARY OF THE INVENTION

It is therefore the objective of this invention to provide a method of processing *Zingiber zerumbet* for producing a processed sample of *Zingiber zerumbet*, which easily releases flavonoids in a following extraction process.

One embodiment of the invention discloses a method of processing *Zingiber zerumbet* including the steps of: soaking a raw sample of *Zingiber zerumbet* with a processing reagent selected from rice vinegar or yellow wine at 23-27° C. for 20-28 hours; and steaming the soaked product at $0.6$-$1.4$ $kg/cm^2$, 80-120° C. for 20-40 minutes.

In a preferred form shown, 100 grams of the raw sample of *Zingiber zerumbet* is soaked with 100 mL of the processing reagent.

In a preferred form shown, the raw sample of *Zingiber zerumbet* is a rhizome of *Zingiber zerumbet*.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1A:
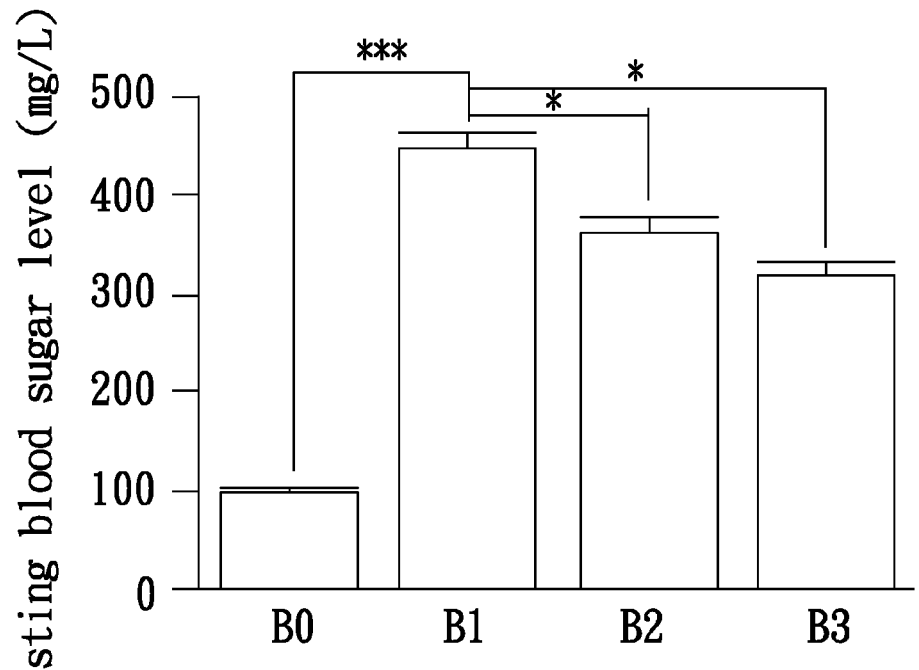
FIG. 1*a* depicts a bar chart showing the fasting blood sugar level in groups B0-B3.

In the various figures of the drawings, the same numerals designate the same or similar parts. Furthermore, when the term "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

A method of processing *Zingiber zerumbet* according to the present invention includes the steps of: soaking a raw sample of *Zingiber zerumbet* with a processing reagent; and steaming the soaked product to obtain a processed sample of *Zingiber zerumbet*.

Specifically, the raw sample indicates a dried rhizome. Further, the processing reagent is selected from rice vinegar or yellow wine.

The raw sample is then soaked with the processing reagent at 23-27° C. for 20-28 hours to obtain the soaked product. In this embodiment, the soaking process is carried out using a sealed container to prevent from contamination of the impurities. Therefore, the processing reagent can penetrate into the raw sample to form the soaked product. For example, in this embodiment, 100 grams of the raw sample is soaked with 100 mL of the processing reagent for 24 hours.

The soaked product is then steamed and the obtained processed sample has a color of light brown. In this embodiment, a pressure cooker set at $0.6$-$1.4$ $kg/cm^2$, 80-120° C. is used for steaming the soaked product for 20-40 minutes.

In order to evaluate the obtained processed sample can easily release flavonoids in a following extraction process, 95% ethanol is used as an extractant to carried out the extraction process. HPLC analysis is then carried out to quantify flavonoids level of the obtained extract.

Trial (A): Release of Flavonoids

The raw sample is soaked with the processing reagent of rice vinegar (group A1, purchased from Taiwan Tobacco & Liquor Corporation) or yellow wine (group A2, purchased from Taiwan Tobacco & Liquor Corporation), followed by steaming to obtain the processed sample of groups A1-A2, respectively. The processed sample (110 grams) is then supersonic extracted with 95% ethanol (5,000 mL) to obtain the extract of groups A1-A2, respectively (extraction 5 times for 99 minutes each times). Moreover, an extract extracted from the raw material is used as a control (group A0).

For analyzing flavonoids, the extract (0.2 grams) is mixed with DMSO (10 mL), followed by ultrasonic vibration for 20 minutes. A filtrate is finally obtained after filtration.

Further, Purospher STAR (purchased from Merck) RP-18e (5 μm) 250 mm×4 mm column is used. A mobile phase for eluting flavonoids includes 40 wt % of acetonitrile and 60 wt % of water. A flow rate of the mobile phase is 1 mL/min. The flavonoids level shown in 254 nm at 35° C. is shown in TABLE 1.

TABLE 1

| Groups | Processing reagent | Flavonoids level (ppm) |
|---|---|---|
| A0 | — | 32363.39 |
| A1 | Rice vinegar | 54009.42 |
| A2 | Yellow wine | 45936.35 |

Referring to TABLE 1, compared to flavonoids level of the extract in group A0, flavonoids level of the extracts in groups A1-A2 shows significant increase, especially flavonoids level of the extract in group A1. That is, the method of processing *Zingiber zerumbet* according to the present invention can be used for producing the processed sample of *Zingiber zerumbet*, which easily releases flavonoids in a following extraction process.

Trial (B): Influence on Blood Markers

Wistar male rats (8-10 week-old, weight 200-250 g) purchased from BioLASCO Taiwan Co., LTd are used in trial (B). The rats are housed in an animal room in the Experimental Animal Center of Tajen university with constant temperature of 25±1° C., where is kept on a 12-hours light and 12-hours dark cycle. The rats are housed and kept on free diet and water.

Rats with type I diabetes (groups B1-B3 shown in TABLE 2) are induced by administration of streptozotocin (STZ, 60 mg/kg) via intraperitioneal injection after fasting for 72 hours. Moreover, after administration of STZ for 72 hours, the rats with type I diabetes show blood sugar level higher than 300 mg/L and symptoms including frequent urination, increased thirst and increased hunger.

Referring to TABLE 2, rats of groups B1-B4 are orally administered with the extract of group A1 for 8 weeks days. The fasting blood sugar level and HbA1c level are measured on day 56.

TABLE 2

| Groups | STZ induction | Treatment (dosage per day) |
|---|---|---|
| B0 | — | Water (1 mL/kg) |
| B1 | + | Water (1 mL/kg) |
| B2 | + | The extract of group A1 (20 mg/kg) |
| B3 | + | The extract of group A1 (40 mg/kg) |

Figure 1B:
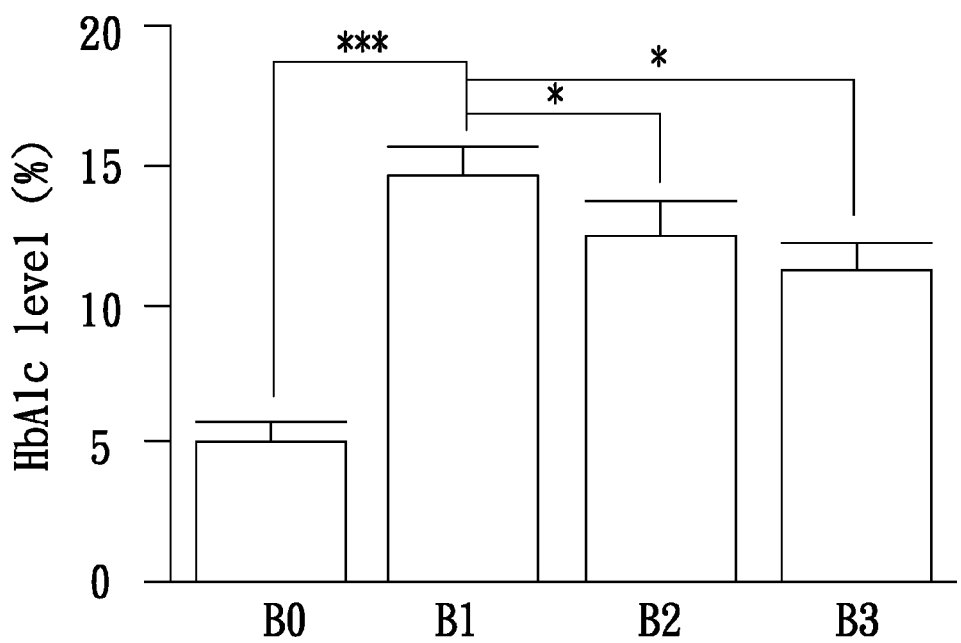
FIG. 1*b* depicts a bar chart showing the HbA1c level in groups B0-B3.

Referring to FIG. 1a, administering the extract of group A1 for 8 weeks decreases the fasting blood sugar level, as well as the HbA1c level shown in FIG. 1b.

Trial (C): Influence on Wound Healing

Referring to TABLE 3, the said rats with type I diabetes are used in trial (C). Full-thickness skin wound with a diameter of 1 cm is formed on the rats of groups C0-C3. In addition, the extract of groups A0 or A1 is plastered to the wound for 3 days. The wound healing percentage is monitored on day 3. Moreover, the wound plastered with silver sulfadiazine is used as a control (group C4).

TABLE 2

| Groups | STZ induction | Treatment (dosage per day) |
|---|---|---|
| C0 | — | — |
| C1 | + | — |
| C2 | + | The extract of group A0 (0.1 mg/cm$^2$) |
| C3 | + | The extract of group A1 (0.1 mg/cm$^2$) |
| C4 | + | Silver sulfadiazine (0.1 mg/cm$^2$) |

Figure 2:
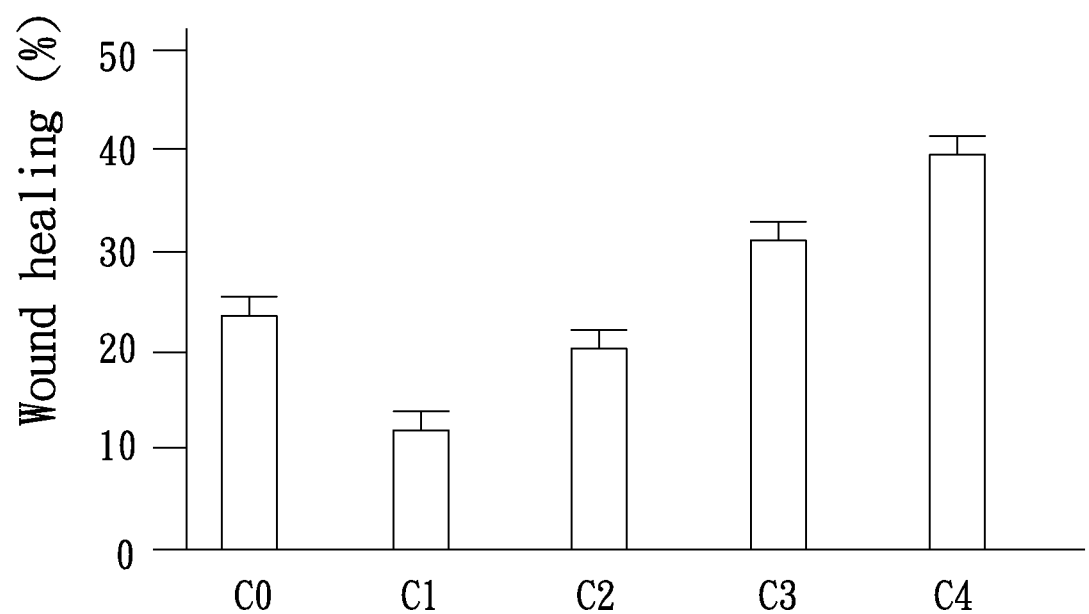
FIG. 2 depicts a bar chart showing the wound healing percentage in groups C0-C4.

Referring to FIG. 2, the extract of group A1 shows effects on wound healing, which is better than the extract of group A0.

Accordingly, by carrying out the method of processing *Zingiber zerumbet*, the obtained processed sample can easily release flavonoids in the following extraction process.

Moreover, with the improved flavonoids level, the extract therefore can be applied to manufacturing a medication for diabetes and its complication.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method of processing *Zingiber zerumbet* consisting of the steps of:

soaking a raw sample of *Zingiber zerumbet* with a processing reagent selected from rice vinegar or yellow wine at 23-27° C. for 20-28 hours to obtain a soaked product; and steaming the soaked product at 0.6-1.4 kg/cm$^2$, 80-120° C. for 20-40 minutes.

2. The method of processing *Zingiber zerumbet* as claimed in claim 1, wherein 100 grams of the raw sample of *Zingiber zerumbet* is soaked with 100 mL of the processing reagent.

3. The method of processing *Zingiber zerumbet* as claimed in claim 1, wherein the raw sample of *Zingiber zerumbet* is a rhizome of *Zingiber zerumbet*.

* * * * *